US008603177B2

(12) United States Patent  
Gray

(10) Patent No.: US 8,603,177 B2
(45) Date of Patent: *Dec. 10, 2013

(54) INTERBODY IMPLANT

(75) Inventor: Wayne P. Gray, Pflugerville, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/397,154

(22) Filed: Feb. 15, 2012

(65) Prior Publication Data

US 2012/0150302 A1 Jun. 14, 2012

Related U.S. Application Data

(63) Continuation of application No. 11/697,108, filed on Apr. 5, 2007, now Pat. No. 8,163,026.

(51) Int. Cl.
A61F 2/44 (2006.01)
A61F 2/00 (2006.01)
A61B 17/60 (2006.01)

(52) U.S. Cl.
USPC .......................................... 623/17.16; 606/99

(58) Field of Classification Search
USPC ............................... 606/99; 623/17.11–17.16
See application file for complete search history.

(56) References Cited

U.S. PATENT DOCUMENTS

| | | | |
|---|---|---|---|
| 5,397,364 A | 3/1995 | Kozak et al. | |
| 5,545,229 A | 8/1996 | Parsons et al. | |
| 5,899,941 A | 5/1999 | Nishijima et al. | |
| 6,387,130 B1 | 5/2002 | Stone et al. | |
| 6,648,916 B1 | 11/2003 | McKay | |
| 7,070,621 B2 | 7/2006 | Castro et al. | |
| 7,534,265 B1 | 5/2009 | Boyd et al. | |
| 7,591,853 B2 | 9/2009 | Felt et al. | |
| 7,763,079 B2 | 7/2010 | McKay | |
| 2003/0125739 A1 | 7/2003 | Bagga et al. | |
| 2003/0139812 A1 | 7/2003 | Garcia et al. | |
| 2005/0033435 A1 | 2/2005 | Belliard et al. | |
| 2005/0107881 A1 | 5/2005 | Alleyne et al. | |
| 2005/0222683 A1 | 10/2005 | Berry | |
| 2006/0058807 A1 | 3/2006 | Landry et al. | |
| 2006/0173542 A1 | 8/2006 | Shikinami | |
| 2006/0259144 A1 | 11/2006 | Trieu | |
| 2008/0119853 A1 | 5/2008 | Felt et al. | |
| 2008/0133017 A1 | 6/2008 | Beyar et al. | |
| 2009/0276047 A1 | 11/2009 | Felt et al. | |
| 2010/0057144 A1 | 3/2010 | Felt et al. | |

FOREIGN PATENT DOCUMENTS

WO 2006051547 A2 5/2006

Primary Examiner — Anu Ramana
(74) Attorney, Agent, or Firm — Seager, Tufte & Wickhem, LLC

(57) ABSTRACT

An interbody implant (20) includes first and second members (22, 24) that are configured to allow the members (22, 24) to be inserted into a disc space separately and then connected together in the disc space to form the interbody implant (20). This allows for a larger interbody implant (20) because the combined size of the members (22, 24) can exceed the size of an access opening into the disc space, with each of the members (22, 24) being sized to pass separately through the access opening before being connected together in the disc space.

20 Claims, 8 Drawing Sheets

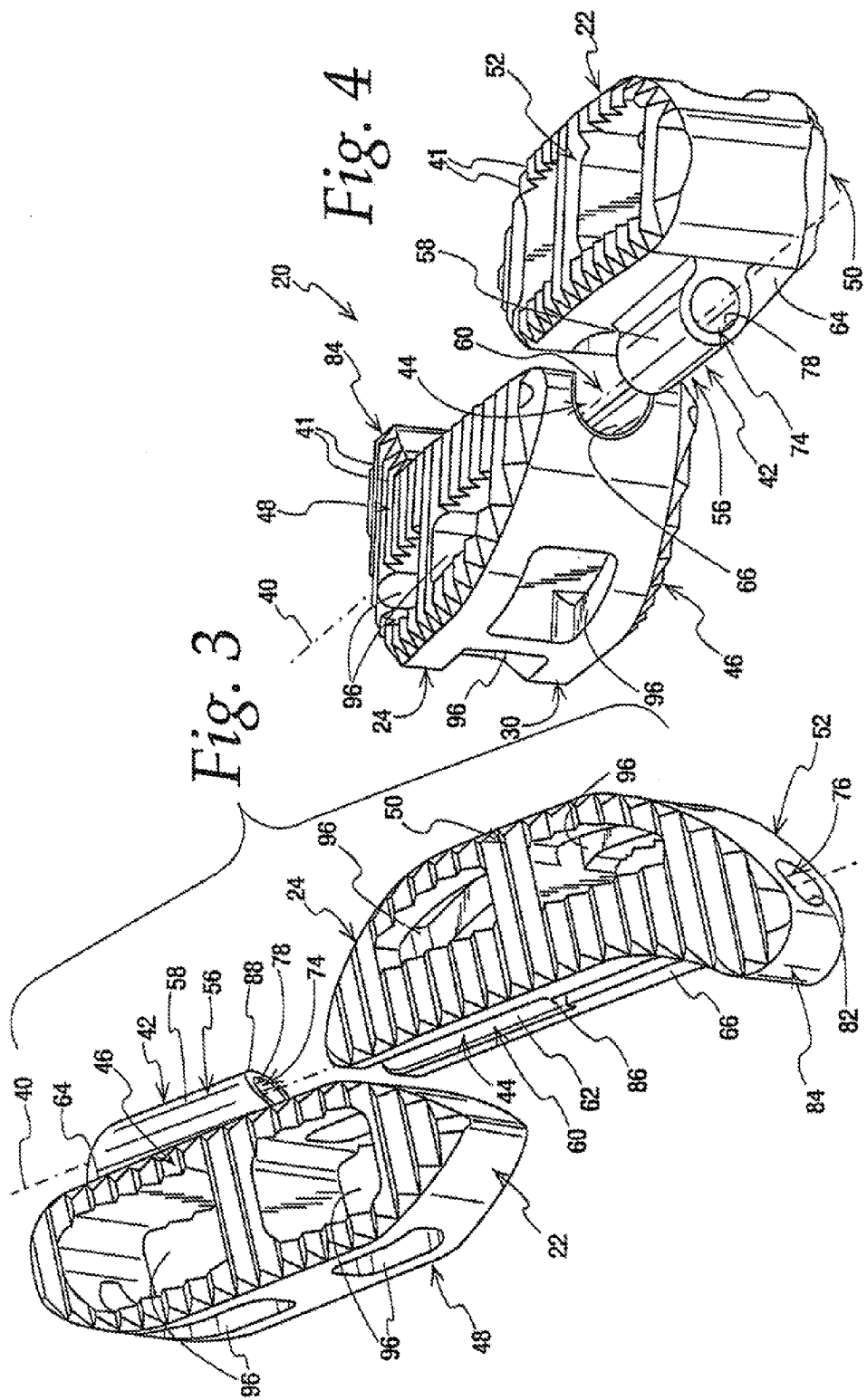

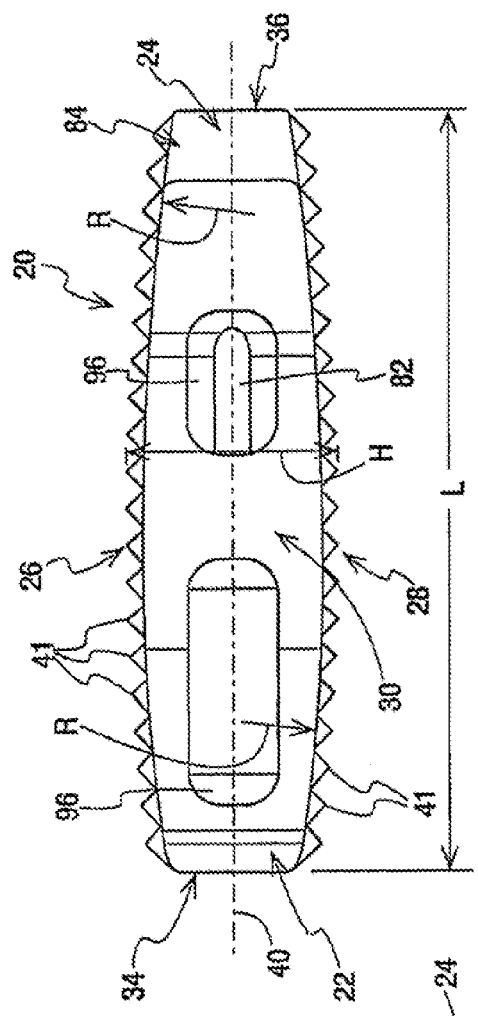
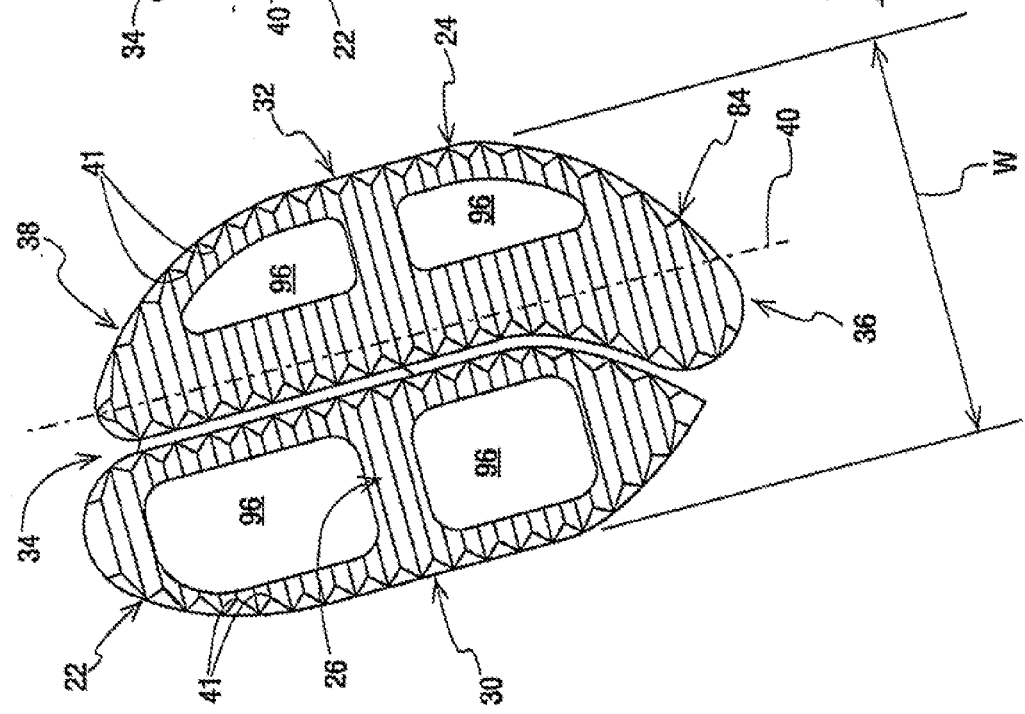

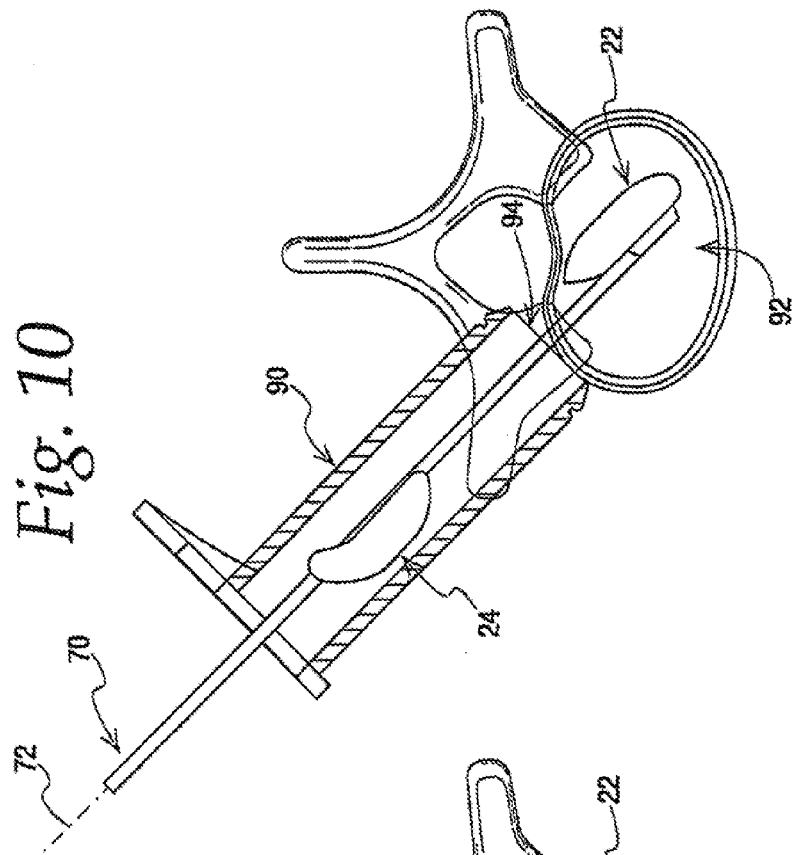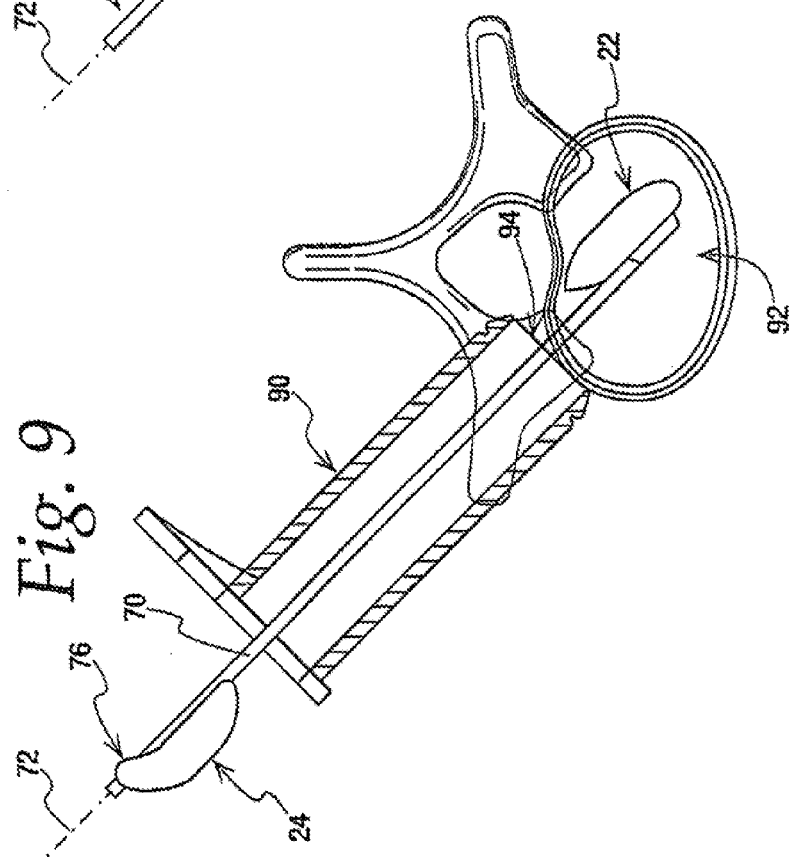

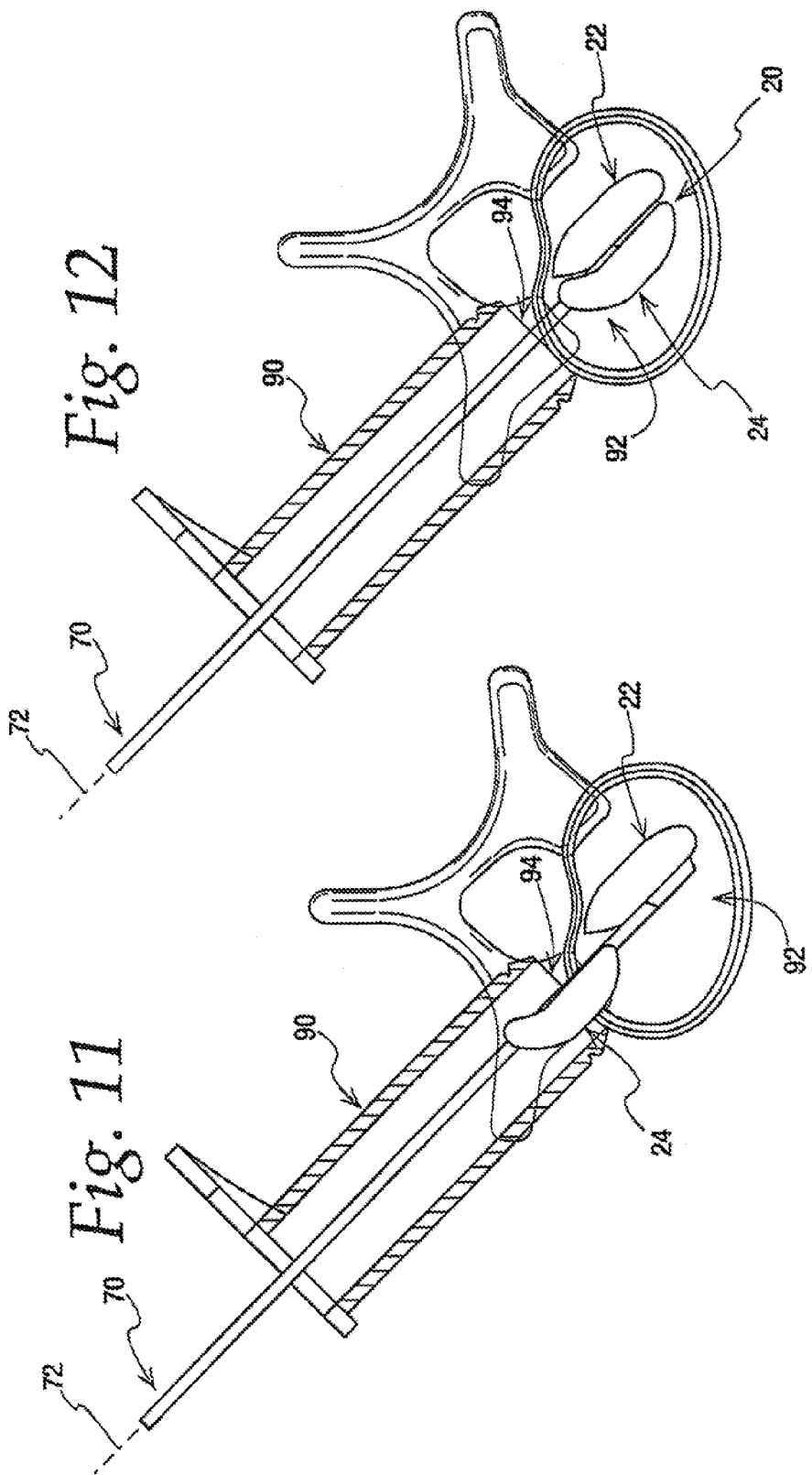

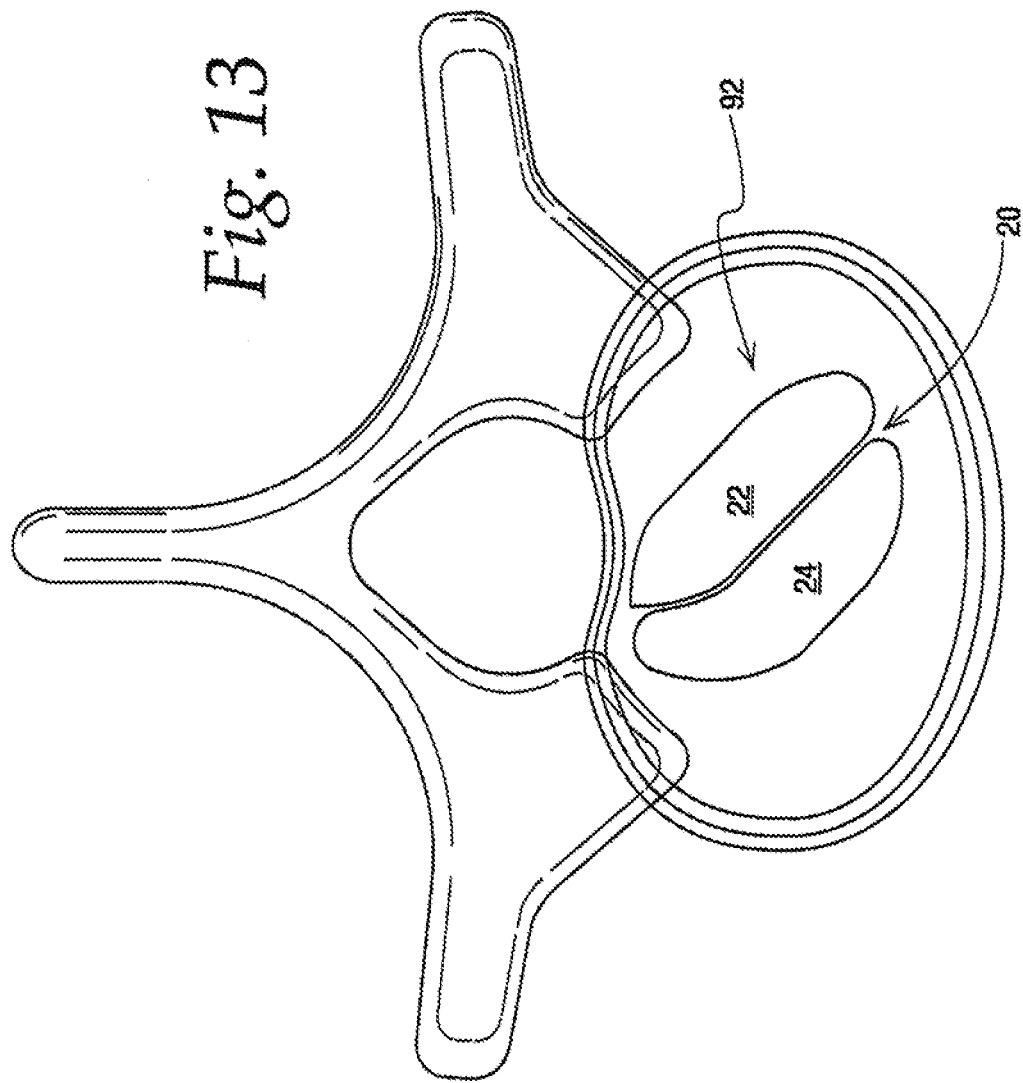

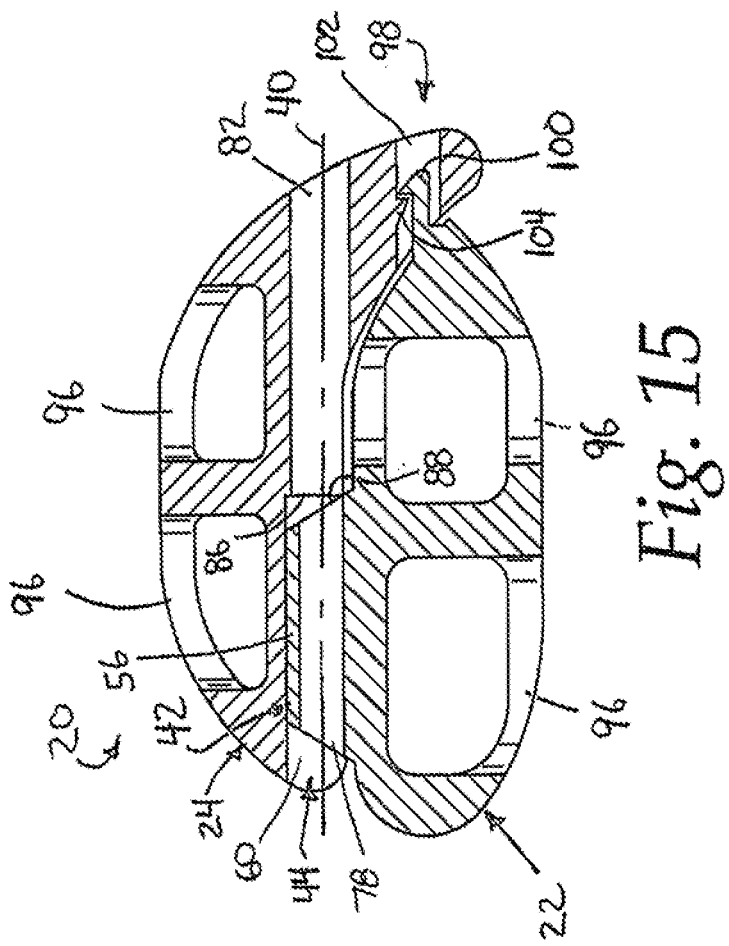
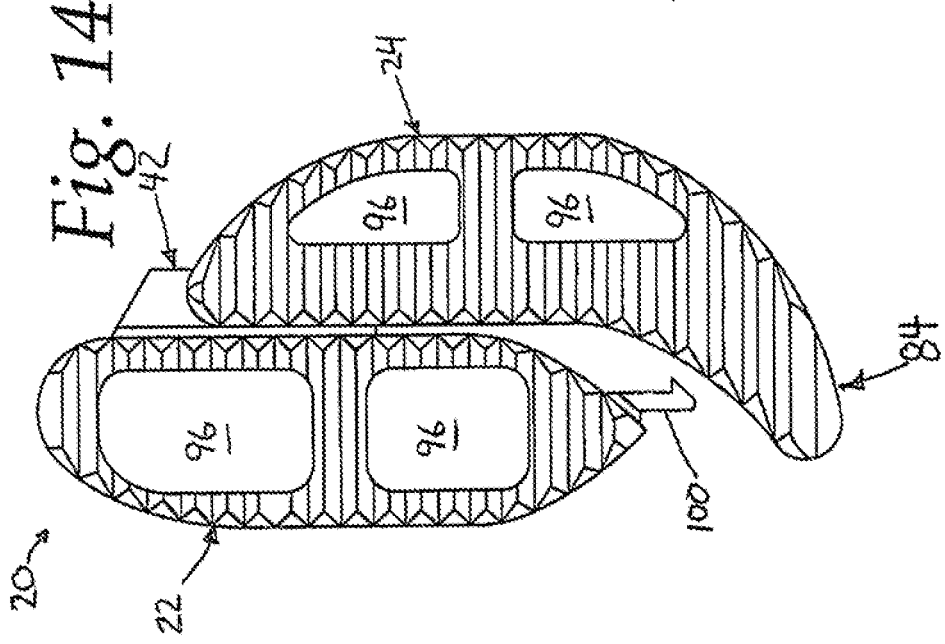

INTERBODY IMPLANT

CROSS-REFERENCE TO RELATED APPLICATIONS

This application is a continuation of U.S. patent application Ser. No. 11/697,108, filed on Apr. 5, 2007 now U.S. Pat. No. 8,163,026, the entire disclosure of which is incorporated herein by reference.

FIELD OF THE INVENTION

The present invention generally relates to the field of bone implants and, in more particularly applications, to spinal interbody implants. Some embodiments of the invention relate to spinal interbody implants inserted into patients during surgical procedures. Some embodiments of the invention relate to methods of inserting an interbody implant during surgery. Spinal interbody implant embodiments may stabilize and/or fuse together vertebrae.

BACKGROUND OF THE INVENTION

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebrae. Maintaining the natural separation between vertebrae may prevent pressure from being applied to nerves that pass between vertebral bodies. Excessive pressure applied to the nerves may cause pain and/or nerve damage. During a spinal fixation procedure, a spinal implant may be inserted within a space created by the removal or partial removal of an intervertebral disc between adjacent vertebrae. The spinal implant may maintain the height of the spine and restore stability to the spine. Bone growth may fuse the implant to adjacent vertebrae.

A spinal implant may be inserted during a spinal fixation procedure using an anterior, lateral, posterior, or translateral, or transverse spinal approach. A discectomy may be performed to remove or partially remove a defective or damaged intervertebral disc. The discectomy creates a disc space for a spinal implant. The amount of removed disc material may correspond to the size and type of spinal implant to be inserted.

Spinal surgery may be complex due in part to the proximity of the spinal cord and/or the cauda equina. Preparation instruments and spinal implants may need to be carefully inserted to avoid damage to nerve tissue. In this regard, the size of the access opening into the disc space may be somewhat limited, which will also limit the size of the spinal implant that may be inserted through the access opening into the disc space.

Bone graft and/or bone implants may be used to promote bone growth that will fuse vertebrae together. Bone graft may be autogenic bone, allogenic bone, synthetic material, xenogenic bone or combinations thereof. Autogenic bone is bone obtained from another location of a patient. Allogenic bone is bone derived from the same species as the patient. Xenogenic bone is bone derived from a species other than that of the patient. Implants may be formed of metal, polymers, ceramics, inorganic compositions, autogenic bone, allogenic bone, xenogenic bone, or combinations thereof.

SUMMARY OF THE INVENTION

In accordance with one feature of the invention, a spinal interbody implant is provided for use with an insertion tool having a longitudinal axis. The implant includes first and second members. The first member includes an attachment portion configured to releasably fix the first member to the insertion tool. The first member further includes a connection portion. The second member includes a guide portion configured for sliding engagement with the insertion tool for movement along the longitudinal axis relative to the insertion tool. The second member further includes a connection portion configured to engage the connection portion of the first member as the second member slides along the insertion tool relative to the first member.

In one feature, the attachment portion includes a threaded opening in the first member.

As one feature, the connection portions include first and second cylindrical surfaces.

According to one feature, the first and second members include a pair of stop surfaces. The stop surfaces abut each other with the connection portions engaged to prevent relative movement in one direction along the longitudinal axis between the first and second members.

In one feature, the attachment portion is a threaded opening formed in the connection portion of the first member.

As one feature, the connection portions include a pair of mating cylindrical surfaces. As a further feature, the connection portion of the first member includes a cylindrically shaped rib and the connection portion of the second member includes a cylindrically shaped groove shaped to receive the rib. In yet a further feature, the guide portion includes the cylindrically shaped groove. As a further feature, the attachment portion includes a threaded opening formed in the cylindrically shaped rib.

According to one feature, the first and second members each have a pair of oppositely facing vertebra contact surfaces, and each of the vertebra contact surfaces has a convex shape. As a further feature, each of the vertebra contact surfaces includes one or more protrusions configured to contact a vertebra.

In accordance with one feature of the invention, a spinal interbody implant includes first and second members, with each member having a laterally facing connection portion located between a pair of oppositely facing vertebra contact surfaces. The connection portions of the first and second members are configured to engage and disengage from each other in response to relative motion between the first and second members along a longitudinal axis.

In one feature, the first and second members include a pair of stop surfaces, with the stop surfaces abutting each other with the connection portions engaged to prevent relative movement in one direction along the longitudinal axis between the first and second members.

As one feature, the connection portions include a pair of mating cylindrical surfaces.

According to one feature, the connection portion of the first member includes a cylindrically shaped rib and the connection portion of the second member includes a cylindrically shaped groove shaped to receive the rib. As a further feature, the cylindrically shaped groove defines a guide portion for sliding engagement with an insertion tool. As a further feature, the implant includes a threaded opening in the cylindrical rib to receive a threaded end of an insertion tool.

In accordance with one feature of the invention, a method is provided for inserting an interbody implant through an access opening into a disc space. The method includes the steps of: inserting a first member into the disc space through the access opening; inserting a second member into the disc space through the access opening, and connecting the first and second members to each other in the disc space to form an interbody insert.

As one feature, the connecting step further includes connecting the first and second members to form an interbody implant that is too large to fit through the access opening.

According to one feature, the method further includes the step of translating the first member to one side of the disc space after the step of inserting the first member and before the step of inserting the second member.

In one feature, the step of inserting the second member includes sliding the second member along an insertion tool.

As one feature, the connecting step includes sliding the second member along the insertion tool while holding the first member in place with the insertion tool.

According to one feature, the method further includes the step of disengaging the insertion tool from the first member after the connecting step.

Other objects, features, and advantages of the invention will become apparent from a review of the entire specification, including the appended claims and drawings.

BRIEF DESCRIPTION OF THE DRAWINGS

FIG. 3 is an exploded perspective view of the interbody implant of FIGS. 1 and 2, again from above and taken from a different angle;

FIG. 4 is an exploded perspective view of the interbody implant of FIGS. 1-3, taken from the opposite end with the implant flipped over to show its underside and at a different angle than FIG. 3;

FIG. 5 is a plan view of the interbody implant of FIGS. 1-4;

FIG. 6 is a side elevation taken from line 6-6 in FIG. 1;

FIGS. 7-12 are a series of plan views illustrating the method of inserting the interbody implant into a disc space embodying the invention;

FIG. 13 is a plan view showing the interbody implant in its installed state in a disc space;

FIG. 14 is a plan view similar to that of FIG. 5, but showing another embodiment of the interbody implant; and FIG. 15 is a rotated, mid-line cross section showing the implant of FIG. 14 in an assembled state.

DETAILED DESCRIPTION

Figure 2:
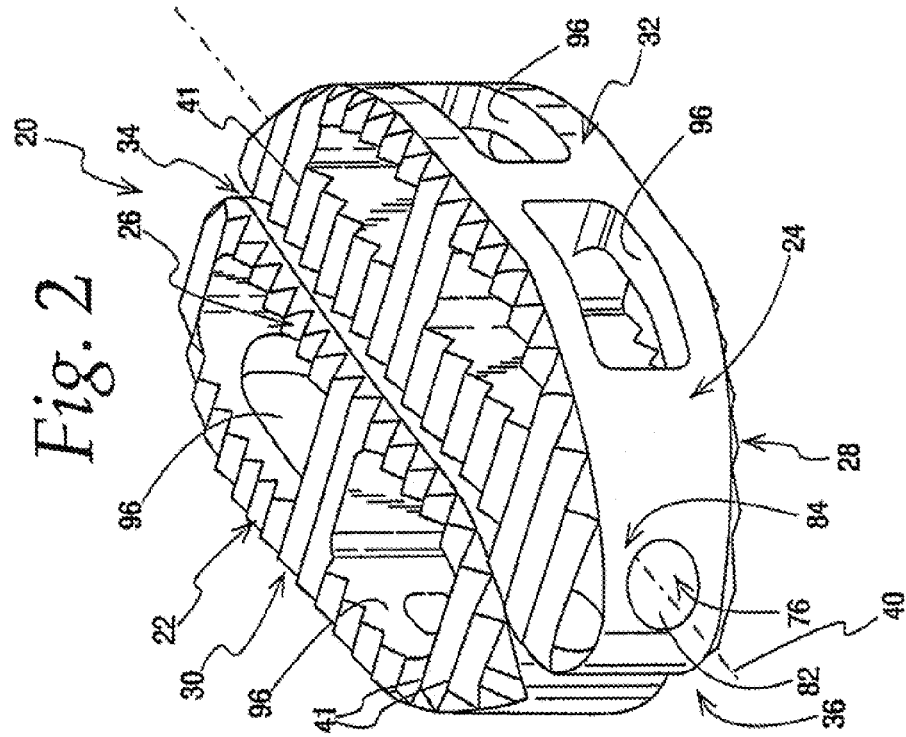
FIG. 2 is a perspective view similar to FIG. 1 of the interbody implant, but taken from a different angle.

With reference to FIGS. 1-6, an interbody implant 20 is shown and includes first and second members 22 and 24 that are configured to allow the members 22 and 24 to be inserted into a disc space separately and then connected together in the disc space to form the interbody implant 20. This allows for a larger interbody implant 20 because the combined size of the members 22 and 24 can exceed the size of an access opening into the disc space, with each of the members 22 and 24 being sized to pass separately through the access opening before being connected together in the disc space. Further, retention of the interbody implant 20 in its desired location/orientation in the disc space is believed to be improved over what otherwise could be obtained if the members 22 and 24 were inserted but not connected to each other.

As best seen in FIGS. 1-2, 5, and 6, in the connected state, the implant 20 has a pair of vertebra engaging faces 26 and 28 spaced from each other by an implant height H, opposite sides 30 and 32 extending between the faces 26 and 28 and spaced from each other by an implant width W, and opposite ends 34 and 36 extending between the faces 26 and 28 and spaced from each other by an implant length L parallel to a longitudinal axis 40. Preferably, as best seen in FIG. 5, the sides 30 and 32 and ends 34 and 36 define a perimeter 38 for the implant 20 that is generally curved and without sharp corners. As best seen in FIG. 6, it is also preferred that the implant height H be tapered along the axis 40 so that the height H is greater in the middle of the implant 20 than at the ends 34 and 36. In this regard, again as best seen in FIG. 6, it is preferred that the each of the faces 26 and 28 have a convex radius of curvature R. While this taper is preferred, in some procedures it may be desirable for there to be no such taper in the implant 20, with the faces 26 and 28 lying in parallel planes to each other over the length L.

It is also preferred that serrations, ridges, or protrusions 41 be provided in each of the faces 26 and 28 to enhance retention of the implant in its desired location/orientation, i.e. to prevent backout. However, in some procedures it may be desirable for there to be no protrusions 41.

Figure 1:
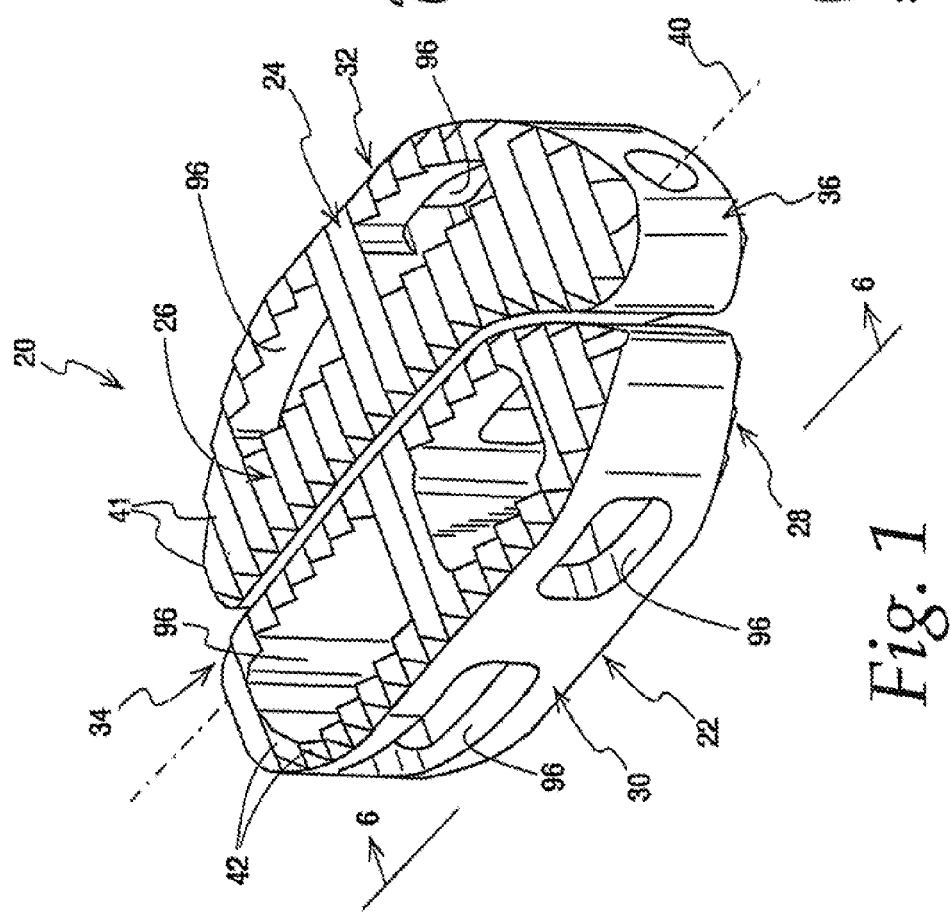
FIG. 1 is a perspective view from above and one end of an interbody implant embodying the present invention.

As best seen in FIGS. 3 and 4, the members 22 and 24 each have a laterally facing connection portion 42 and 44, respectively, with the connection portion 42 being located between a pair of oppositely facing vertebra contact surfaces 46 and 48, and the connection portion 44 being located between a pair of oppositely facing vertebra contact surfaces 50 and 52. As best seen in FIGS. 1 and 6, in the connected state, it is preferred that the surfaces 46 and 50 are aligned with each other to define the face 26, and the surfaces 48 and 52 are aligned with each other to define the face 28. In this regard, as best seen in FIG. 6, it is follows that each of the surfaces 46, 48, 50, and 52 have the convex radius of curvature R and the protrusions 41.

As best seen in FIG. 3, the connection portion 42 includes a cylindrically shaped protrusion or rib 56 having an outwardly facing cylindrical surface 58 and the connection portion 44 includes a cylindrically shaped slot 60 having an inwardly facing cylindrical surface 62, with both the rib 56 and the slot or groove 60 being centered on the axis 40 in the connected state. The rib 56 extends from a planar side surface 64 and the groove 60 is formed in a planar side surface 66. Preferably, the cylindrical surfaces 58 and 62 conform to each other. It should be appreciated that while the cylindrical surfaces 58 and 62 are shown, there are many other possible mating cross-sectional shapes for the rib 56 and groove 60 that can provide a suitable connection between the members 22 and 24, such as, for example, mating dovetail shapes or mating T shapes.

As will be discussed in more detail below, the implant is preferably configured for use with an insertion tool 70, best seen in FIGS. 7-12, having a longitudinal axis 72. In this regard, as best seen in FIGS. 3 and 4, it is preferred that the member 22 include an attachment portion 74 that is configured to releasably fix the first member 22 to the insertion tool 70, and for the member 24 to include a guide portion 76 for sliding engagement of with the insertion tool 70 for movement along the axis 72 relative to the insertion tool 70. In the illustrated embodiment, the attachment portion 74 includes a threaded bore 78 centered in the rib 56 and extending along the axis 40 to engage a threaded end 80 of the insertion tool 70, and the guide portion 76 includes a cylindrical bore 82 extending along the axis 40 and becomes part of the groove 60. It is preferred that the bore 82 be formed in a nose portion 84 of the member 24 that extends laterally past the plane of the surface 66 so that the material of the member 24 completely surrounds the insertion tool 70 over a length of the guide portion 74. However, it should be understood that in some embodiments the nose portion 84 may be eliminated, with the bore 82 having an open portion over its entire length.

The bore 82 has a smaller diameter than the cylindrical surface 62 of the groove 60, which results in an annular shoulder 86 located between the bore 82 and the surface 60, as best seen in FIG. 3. The annular shoulder 86 abuts an end surface 88 of the rib 56 in the connected state to prevent further relative motion between the members 22 and 24 along the axis 40 in the direction of engagement for the connection portions 42 and 44.

The implant 20 according to the invention may be used in minimally invasive surgery/less invasive surgery (MIS/LIS) procedures such as percutaneous transforaminal lumbar interbody fusion (TLIF), posterior lumbar interbody fusion (PLIF), or in non-MIS procedures, as desired, and as persons of ordinary skill in the art who have the benefit of the description of the invention understand. While the implant 20 can be used with any surgical procedure, it is particularly suited for use with MIS Procedures. MIS procedures seek to reduce cutting, bleeding, and tissue damage or disturbance associated with implanting a spinal implant in a patient's body.

In some embodiments, a port 90 may be inserted into a patient to provide access to vertebrae that are to be fused together. Instruments (e.g., distractors, chisels, and implant inserters) may be inserted into the port 90 during an implant insertion procedure. A discectomy may be performed to remove disc material and form a first disc space between two adjacent vertebral bodies. A distractor may be positioned between to establish a separation distance in the disc space between the vertebrae. Further, a chisel may be used to remove portions of vertebral bone and form channels in the vertebral end plates adjacent the disc space. Removing bone portions may promote bone growth that couples an implant inserted in the disc space to the vertebrae. Osteophytes may also be removed to make insertion of the implant easier.

Figure 7:
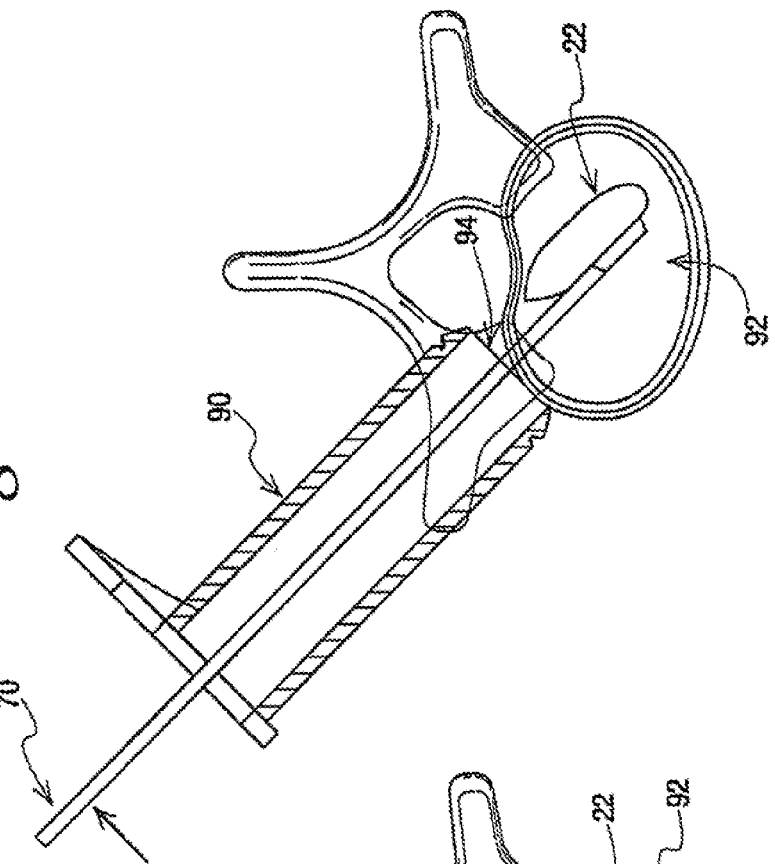
Figure 8:
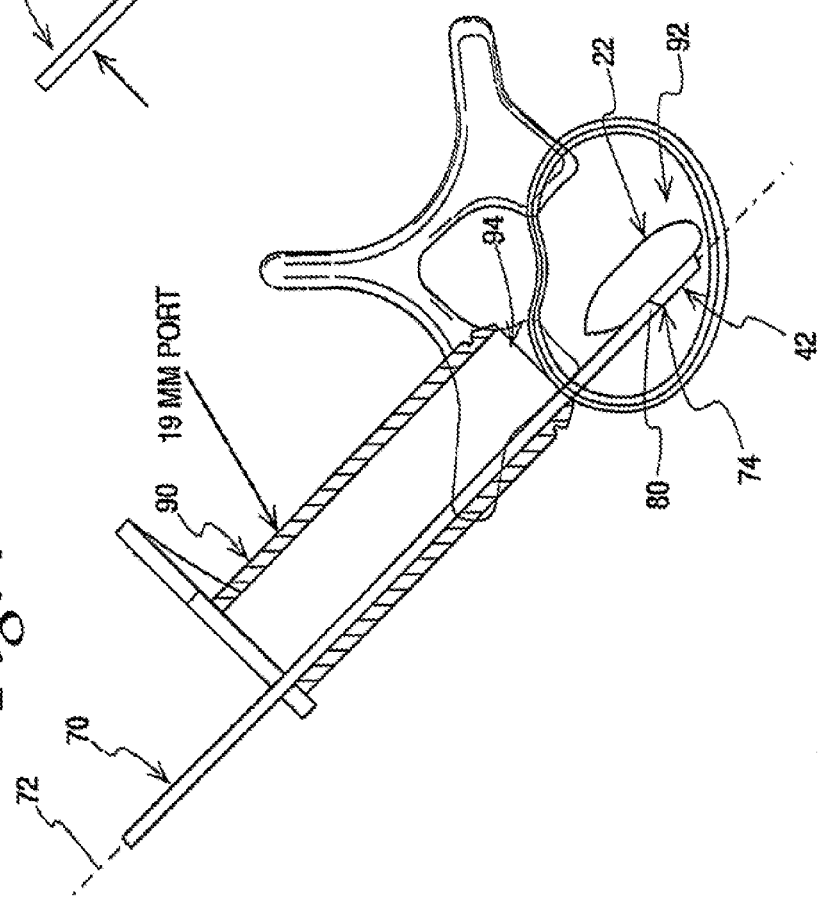

FIGS. 7-13 sequentially illustrate one possible MIS procedure for implanting the implant 20 into a patient. FIG. 7 shows the member 22 attached to the insertion tool 70 by the attachment portion 74 and inserted into a prepared disc space 92 through the port 90 and an access opening 94 to the disc space 92. The access opening 94 to the disc space 92 will typically have a size that essentially corresponds to an interior diameter of the port 90. FIG. 8 shows the next step of the procedure where the member 22 is shifted or translated to one side of the disc space 92 using the insertion tool 90, as indicated by the arrow A. This shift allows for the next step of the procedure shown in FIG. 9-11 wherein the guide portion 76 of the member 24 is engaged with the insertion tool 70 and the member 24 is slid down the tool 70 into the disc space 92 while the member 22 is held in place by the tool 70. Next, as seen in FIG. 12, the connection portions 42 and 44 are engaged to form the implant 20 by sliding the member 24 along the insertion tool 70 while the member 22 is held in place by the tool 70. While not shown, it may be desirable to utilize another tool to slide the member 24 along the tool 70 for the steps of the procedure shown in FIGS. 9-12. Finally, as illustrated in FIG. 13, after the implant 20 is positioned in its desired location/orientation, the insertion tool 70 is disengaged from the attachment portion 74 and withdrawn from the port 90, which is also removed after any further procedures are completed, such as, for example, inserting packing material, such as cancellous bone, synthetic bone, or other bone graft material, in the disc space 92 around the implant 20.

It should be understood that while a translateral approach is shown in FIGS. 7-12, the implant 20 and the described insertion method can be used with any type of approach, including posterior, anterior, and lateral.

It should be understood that while the insertion tool 70 is shown in the form of a cylindrical rod, shapes other than cylindrical are possible. Furthermore, it should be understood that other forms of insertion tools 70 are also possible.

It should be understood that the interbody implant 20 can be used to promote bone fusion and/or establish a desired separation distance between adjacent vertebrae. In some embodiments, the implant 20 may have surfaces made of bone or bone growth promoting material (e.g., hydroxyapatite or titanium plasma spray) that promotes fusion of the implants to vertebrae. In some embodiments, as shown in FIGS. 1-6, the implant 20 may include passages or openings 96. The openings 96 may have any desired cross-sectional shape. For example, the passage cross-sectional shape may be, but is not limited to, circular, oval, square, rectangular, or irregular. The openings 96 may be packed with bone graft or other bone growth material (e.g., autogenic bone graft, allogenic bone graft, xenogenic bone graft, or synthetic bone graft) that promotes bone growth from vertebrae into the implant 20 to fuse the implant 20 to the vertebrae.

It is believed that the pressure of the vertebral bodies on the implant 20 will typically be sufficient to retain the members 22 and 24 in the connected state. However, in some embodiments it may be desirable for there to be a positive retention feature between the connection portions 42 and 44. For example, a threaded fastener could be provided extending through the bore 82 to engage the threaded bore 78 to retain the connection portions 42 and 44 in engagement. As another example, some form of a "snap connection" could be provided between members 22 and 24 to retain the connection portions 42 and 44 in engagement. In this regard, one possible form of a "snap connection" or "snap lock" 98 is shown in FIGS. 14 and 15 wherein the members 22 and 24 of the implant 20 have been modified so that the member 22 includes a somewhat hook-shaped latch 100 extending in cantilevered fashion from one end thereof, and the member 24 includes an opening 102 formed in the nose portion 84, which has been extended in comparison to the embodiment of FIGS. 1-13, with a somewhat wedge-shaped catch 104 formed in the opening 102 to engage the latch 100 as the members 22 and 24 are moved into engagement along the axis 40 and retain the first and second members 22 and 24 in the assembled state, as best seen in FIG. 15. While a preferred form is shown in FIGS. 14 and 15, it will be appreciated by those skilled in the art that there are many possible forms for the latch 100 and catch 104. For example, the latch 100 could have been formed extending from the nose 84 of the member 24, with the opening 102 and catch 104 formed in the end of the member 22.

Implants 20 may be constructed of biocompatible material sufficiently strong to maintain bone separation, and may be made of bone or of other material, such as metals, ceramics, polymers, or combinations thereof. Bone used to form an implant may be allogenic bone or xenogenic bone. In some embodiments, a portion or portions of the implant 20 may be autogenic bone. In some embodiments, bone, or portions of bone, used to form the implant 20 may be demineralized. Portions of the bone used to form the implant 20 may be cortical bone. The cortical bone may provide strength to the implant 20. In some implant embodiments, the bone used to form an implant 20 may be processed in a frozen state. In some implant embodiments, bone used to form the implant 20 may be processed in a freeze-dried state.

In some implant embodiments, the implant 20 and/or outer surfaces of the implant 20 that contact a vertebra may be made of a material other than bone. The surfaces that contacts the vertebra may be treated to enhance osseointegration of the implant with the vertebra. The surfaces may include protrusions that extend into the vertebra. The surface may include a hydroxyapatite coating, a titanium plasma spray coating, and/or texturing. Texturing may be used to modify the surface of an implant to reduce expulsion and provide stability. Texturing may be provided by many different methods, such as, but not limited to, sanding the surface, forming grooves within the surface, shot peening the surface, scoring the surface using an electrical discharge process, and/or embedding hard particles within the surface. Texturing may also be formed in outer surfaces of implants formed of bone.

An implant, or a portion of an implant, may be made of a bioabsorbable material. For example, portions of an implant may be made of a polyanhydride, an alpha polyester, and/or a polylactic acid-polyglycolic acid copolymer.

In some embodiments, the implant 20 may be constructed from bar stock or formed from moldable material of suitable strength to withstand pressure within a normal human spine. For example, the implant 20 may be constructed from metals including, but not limited to, titanium, titanium alloys, and medical grade stainless steel. As a further example, the implant 20 may be molded or cut from materials including, but not limited to, polyether ether ketone (PEEK), carbon fiber reinforced PEEK, and other polymers.

It should be understood that while one possible shape for the members 22 and 24, and the implant 20 have been shown, there are many possible shapes and the particular shape selected will be highly dependent upon the specifics of the procedure and the patient. For example, in some embodiments, the implant 20 may be processed so that posterior side or end, as implanted in a patient, of the implant 20 has a different height H than anterior side or end of the implant 20. Other dimensional characteristics of an implant 20 may also be adjusted to produce an implant having a desired geometry.

What is claimed:

1. A spinal interbody implant for use with an insertion tool having longitudinal axis, the implant comprising:
    a first member including a superior vertebra engaging surface, an inferior vertebra engaging surface, and a laterally facing connection portion located between the superior and inferior vertebra engaging surfaces of the first member; and
    a second member including a superior vertebra engaging surface, an inferior vertebra engaging surface, and a laterally facing connection portion located between the superior and inferior vertebra engaging surfaces of the second member;
    wherein the first member is configured to be secured to a distal portion of the insertion tool for insertion into a disc space between a first vertebra and a second vertebra;
    wherein the connection portion of the second member includes a passage through which the insertion tool slidably passes through as the second member is advanced into the disc space between the first vertebra and the second vertebra while the insertion tool is secured to the first member in the disc space;
    wherein the connection portion of the second member is configured to slide into a channel defined by of the connection portion of the first member to couple the second member with the first member upon insertion of the second member into the disc space; and wherein the insertion tool is separate from and not part of the coupled first and second members.

2. The implant of claim 1, wherein the first and second members include a pair of stop surfaces, the stop surfaces abutting each other once the connection portion of the second member is fully slid into the channel of the connection portion of the first member.

3. The implant of claim 2, wherein the engagement of the pair of stop surfaces prevents further advancement of the second member relative to the first member.

4. The implant of claim 1, wherein the connection portion of the second member includes a cylindrically shaped rib and the channel of the connection portion of the first member is cylindrically shaped to receive the cylindrically shaped rib.

5. The implant of claim 4, wherein the insertion tool extends along the cylindrically shaped channel of the first member.

6. The implant of claim 1, wherein one of the first and second members includes a latch and the other of the first and second members includes a catch that is engageable with the latch to retain the first and second members coupled together.

7. A spinal interbody implant for use with an insertion tool having longitudinal axis, the implant comprising:
    a first member including a superior vertebra engaging surface, an inferior vertebra engaging surface, and a laterally facing connection portion located between the superior and inferior vertebra engaging surfaces of the first member; and
    a second member including a superior vertebra engaging surface, an inferior vertebra engaging surface, and a laterally facing connection portion located between the superior and inferior vertebra engaging surfaces of the second member;
    wherein the first member is configured to be secured to a distal portion of the insertion tool for insertion into a disc space between a first vertebra and a second vertebra;
    wherein the connection portion of the second member includes a passage through which the insertion tool slidably passes through as the second member is advanced into the disc space between the first vertebra and the second vertebra while the insertion tool is secured to the first member in the disc space;
    wherein the connection portion of the second member is configured to slide into a channel defined by the connection portion of the first member to couple the second member with the first member upon insertion of the second member into the disc space;
    wherein each of the superior and inferior vertebra engaging surfaces includes a plurality of protrusions configured to engage a vertebra; and wherein the insertion tool is separate from and not part of the coupled first and second members.

8. The implant of claim 7, wherein the protrusions of the superior vertebra engaging surfaces of the first member are aligned with the protrusions of the superior vertebra engaging surfaces of the second member when the first and second member are coupled together.

9. The implant of claim 8, wherein the protrusions of the inferior vertebra engaging surfaces of the first member are aligned with the protrusions of the inferior vertebra engaging surfaces of the second member when the first and second member are coupled together.

10. The implant of claim 7, wherein the protrusions of the inferior vertebra engaging surfaces of the first member are aligned with the protrusions of the inferior vertebra engaging surfaces of the second member when the first and second member are coupled together.

11. A spinal interbody implant for use with an insertion tool having longitudinal axis, the implant comprising:
    a first member including a superior vertebra engaging surface, an inferior vertebra engaging surface, and a laterally facing connection portion located between the superior and inferior vertebra engaging surfaces of the first member; and a second member including a superior vertebra engaging surface, an inferior vertebra engaging surface, and a laterally facing connection portion located between the superior and inferior vertebra engaging surfaces of the second member;

wherein the first member is configured to be secured to a distal portion of the insertion tool for insertion into a disc space between a first vertebra and a second vertebra;

wherein the connection portion of the second member includes a passage through which the insertion tool slidably passes through as the second member is advanced into the disc space between the first vertebra and the second vertebra while the insertion tool is secured to the first member in the disc space; and wherein the connection portion of the second member is configured to slide into a channel defined by the connection portion of the first member to couple the second member with the first member upon insertion of the second member into the disc space; and wherein the first member includes a threaded opening for threadably receiving the distal portion of the insertion tool.

12. A method for inserting an interbody implant through an access opening into a disc space between first and second vertebrae, the method comprising the steps of:

inserting a first member of the interbody implant into the disc space between the first and second vertebrae with an insertion tool attached to the first member, the first member including a superior vertebra engaging surface for engaging the first vertebra, an inferior vertebra engaging surface for engaging the second vertebra, and a laterally facing connection portion located between the superior and inferior vertebra engaging surfaces of the first member;

with the first member positioned in the disc space, inserting a second member into the disc space between the first and second vertebrae by sliding the second member along the insertion tool attached to the first member, the second member including a superior vertebra engaging surface for engaging the first vertebra, an inferior vertebra engaging surface for engaging the second vertebra, and a laterally facing connection portion located between the superior and inferior vertebra engaging surfaces of the second member;

wherein the insertion tool slidably passes through a passage of the connection portion of the second member as the second member is advanced into the disc space between the first vertebra and the second vertebra while the insertion tool is attached to the first member in the disc space;

sliding the connection portion of the second member into a channel of the connection portion of the first member to couple the second member with the first member upon insertion of the second member into the disc space; and removing the insertion tool from the first and second members such that the insertion tool is separate from and not part of the coupled first and second members.

13. The method of claim 12, wherein the interbody implant that is assembled in the disc space has a width that is larger than the access opening.

14. The method of claim 12, further comprising the step of: translating the first member to one side of the disc space after the step of inserting the first member and before the step of inserting the second member.

15. The method of claim 12, further comprising the step of: disengaging the insertion tool from the first member after the step of inserting the second member.

16. The method of claim 12, wherein the first member includes a threaded opening for threadably receiving the distal portion of the insertion tool.

17. The method of claim 12, wherein the first and second members include a pair of stop surfaces, the stop surfaces abutting each other once the connection portion of the second member is fully slid into the channel of the connection portion of the first member.

18. The method of claim 17, wherein the engagement of the pair of stop surfaces prevents further advancement of the second member relative to the first member.

19. The method of claim 12, wherein the connection portion of the second member includes a cylindrically shaped rib and the channel of the connection portion of the first member is cylindrically shaped to receive the cylindrically shaped rib.

20. The method of claim 19, wherein the insertion tool extends along the cylindrically shaped channel of the first member.

* * * * *